United States Patent [19]

Brown

[11] Patent Number: 5,151,412
[45] Date of Patent: Sep. 29, 1992

[54] PHARMACEUTICALLY ACTIVE CONJUGATES HAVING IMPROVED BODY TISSUE BINDING SPECIFICITY

[75] Inventor: Robert A. Brown, St. Albans, Great Britain

[73] Assignee: Central Blood Laboratories Authority, Borehamwood, Great Britain

[21] Appl. No.: 359,662
[22] PCT Filed: Nov. 27, 1987
[86] PCT No.: PCT/GB87/00854
§ 371 Date: Jul. 21, 1989
§ 102(e) Date: Jul. 21, 1989
[87] PCT Pub. No.: WO88/03810
PCT Pub. Date: Jun. 2, 1988

[30] Foreign Application Priority Data

Nov. 27, 1986 [GB] United Kingdom ............... 8628398

[51] Int. Cl.$^5$ .............. A61K 37/12; A61K 47/48; A61K 37/14; C07K 17/02
[52] U.S. Cl. ........................... 514/8; 530/363; 530/380; 530/382; 530/391.9; 530/395; 530/400; 514/2; 514/6; 514/21; 424/85.91; 435/177
[58] Field of Search ............... 514/8, 2, 6, 21; 424/85.91; 530/380, 395, 390, 391, 363, 391.9, 400, 812, 382; 435/177

[56] References Cited

U.S. PATENT DOCUMENTS

| | | | |
|---|---|---|---|
| 4,046,722 | 9/1977 | Rowland | 530/362 |
| 4,560,556 | 12/1985 | Kagitani et al. | 424/101 |
| 4,587,122 | 5/1986 | Kagitani | 424/101 |
| 4,589,881 | 5/1986 | Pierschbacher et al. | 623/11 |

FOREIGN PATENT DOCUMENTS

| | | |
|---|---|---|
| 0114685 | 8/1984 | European Pat. Off. . |
| 0134320 | 3/1985 | European Pat. Off. . |
| 2119804 | 11/1983 | United Kingdom . |
| 86/01720 | 3/1986 | World Int. Prop. O. . |

OTHER PUBLICATIONS

Blair et al. (1983) J. Immunol. Methods 59c 129–143.
Pierschbacher et al. (1984) Nature 309:30–33.
Hynes, R. O. et al., *J. Cell Biol.*, 95, 369–377 (1982) "Fibronectins: multifunctional modular glycoproteins".
Hahn, L-H. E. et al., *Cell*, 18, 1043–1051 (1979) "Isolation and Biological Characterization of Active Fragments in the Adhesive Glycoprotein in Fibronectin".
Mosesson, M. W. et al., in Plasma Fibronectin ed. J. McDonagh, Marcel Dekker In., N.Y., 1985 Chaper 5: "Interactions with Glycosaminoglycans".
Hörmann, H. in Plasma Firbonectin, ed J. McDonagh, Marcel Dekker Inc., No. 1985, Chapter 6, "Interactions with Fibrinogen and Fibrin" pp. 99–120.

Primary Examiner—Christine M. Nucker
Assistant Examiner—Kay K. Kim
Attorney, Agent, or Firm—Foley & Lardner

[57] ABSTRACT

Pharmaceutically active conjugates comprising a pharmaceutically active substance for treating a disorder of the body that involves a specified body tissue conjugated directly or indirectly with at least one fragment of an adhesive glycoprotein such as fibronectin, the said glycoprotein fragment(s) having improved binding specificity compared with the parent protein for the said body tissue.

18 Claims, 3 Drawing Sheets

PHARMACEUTICALLY ACTIVE CONJUGATES HAVING IMPROVED BODY TISSUE BINDING SPECIFICITY

This invention relates to pharmaceutically active conjugates having improved binding specificity for specified body tissue. The invention further relates to methods of preparing these conjugates and to pharmaceutical preparations that contain them. In particular embodiments, the invention relates to pharmaceutically-active conjugates containing either plasminogen activators or anti-rheumatic drugs.

It is common practice to administer large doses of various drugs to the body to treat conditions which may only affect a small region of the body. Large doses are often required in order to attain a sufficient concentration of the drug at the target area. However, these large and constantly-administered doses can produce serious side effects in patients being treated, which has often lead to treatment being suspended even though improvement in the treated condition might be taking place. This problem has existed in the past particularly in the administration of toxic anti-tumour drugs for destroying cancer cells and in the administration of toxic anti-rheumatic drugs, especially gold compounds.

One further example of the administration of drugs where this problem exists is in the treatment of thrombotic conditions. Conventional treatment for certain thrombotic conditions, such as deep vein thrombosis or pulmonary thrombosis, involves continuous infusion of agents which stimulate fibrinolysis Fibrinolysis is the term given to the process of proteolytic degradation of a fibrin-based clot. Thrombolysis is the plasmin mediated proteolysis which brings about the break up of large vascular obstructions. It is generally accepted that the main enzyme responsible for fibrinolysis is plasminogen-plasmin. The zymogen, plasminogen, is converted by one of a range of activators to plasmin, which is an active protease capable of degrading a cross-linked fibrin clot to soluble products (FDPs). Plasmin is a serine protease, produced from plasminogen by limited proteolytic cleavage accompanied by a conformational change.

The precise mechanism of plasminogen activation depends on the plasminogen activator involved. Thus, activation can also occur without proteolytic cleavage in the case of plasminogen activators from certain microorganisms which act allosterically, e.g. streptokinase. In general activation is more effective if it occurs on the surface of the clot, a phenomenon aided by the affinity that plasminogen has for fibrin. Plasminogen activators occur in blood, a variety of tissues and in body fluids such as urine, saliva and semen. As hereinbefore indicated, they are also produced by certain microorganisms. Small quantities of a labile plasminogen activator, tissue plasminogen activator (t-PA), occur in the circulation. Its level is raised following stimuli including exercise and venous occlusion. t-PA, which carries a fibrin-binding region, has been isolated from cadaveric plasma and from culture medium of vascular endothelial cells and the Bowes melanoma cell line. More recently, this plasminogen activator has also been prepared by recombinant DNA technology (see, for example, GB-A No. 2119804).

Urokinase (UK) is a plasminogen activator present in urine. Unlike t-PA, it can be readily isolated in a highly purified, crystalline form. It is a single chain β-globulin which exists in two forms of molecular weights 54,000 and 32,000 respectively. UK is (apparently) synthesised in the kidney and, unlike t-PA, it has little affinity for fibrin. UK activates plasminogen to produce plasmin which is subject to inhibition.

Streptokinase (SK) is a plasminogen activator produced by β-haemolytic streotococci and available in purified preparations. SK is a single chain α2-globulin having a molecular weight around 46,000. It acts as an activator by binding to plasminogen causing a conformational change. The resultant SK-plasminogen complex possesses enzymic activity, but is not inhibited by α2-macroglobulin.

Both UK and SK have been used successfully as thrombolytic agents. SK is more commonly used since it is cheaper to produce, although UK is generally regarded as a better agent. SK is highly antigenic and tends to be effective for only one treatment, after which the number of antibodies raised by the body's autoimmune system render subsequent treatments much less effective. In addition, the titre of anti-SK antibodies varies between individuals depending on the previous history of Streptococcal infections. This makes it difficult to determine the effective safe dose. Antibody mediated resistance does not occur with UK.

Although UK has no antigenicity, UK therapy suffers from the dual disadvantages of limited availability and high cost, consequent on the need to fractionate very large volumes of human urine. The huge dose of UK necessary to maintain a thrombolytic state is thought to be partly due to its poor affinity for fibrin. The result is that a complete course of treatment requires the fractionation of around 5000 liters of urine. In the case of both UK and SK therapy, there is a serious risk of haemorrhagic complication due to the systemic administration of large doses of activator. Attempts to achieve thrombolysis by local administration have not been encouraging. In the case of SK, it is thought that effective and haemorrhagic doses are almost the same, so that an effective dose can cause hyperplasminaemia, fibrinogen degradation, and an accumulation of fibrinogen degradation products which have an anticoagulant effect and so add to haemorrhagic complications.

More recently, attempts have been made to overcome this problem by linking drugs to carriers which have a high affinity for the area of the body requiring treatment. These carriers target the drug on to the area requiring treatment and can thereby be administered in relatively low but still effective doses. Examples of such carriers are disclosed in published patent specifications EP-A No. 2-114685 and, more recently, U.S. Pat. No. 4,587,122, which describe the preparation and use of various anti-tumour, anti-bacterial and anti-inflammatory drugs covalently conjugated with whole fibronectin (an adhesive glycoprotein) using protein cross-linking agents. Although fibronectin is claimed to be an effective carrier which binds readily to morbid regions of the body where treatment by drugs might be required, fibronectin itself carries binding sites for a large number of body tissues and so preferential binding to a site of the body requiring treatment cannot be guaranteed; indeed, preferential binding may occur in other parts of the body in which case the amount of drug accumulating in the area requiring treatment may in some cases be negligible. Furthermore, there is some evidence to suggest that fibronectin normally accumulates at sites within the body by self-association on to initial, bound fibronectin. That is to say, self-association leads to non-specific amplification of fibronectin accumulation. Clearly, this mechanism would severely impair the "targetting" ability of administered fibronectin-drug conjugates since they could bind to any site of fibronectin accumulation within the body.

The present invention is based on the concept of providing improved drug conjugates having targetting portions which have a higher relative degree of binding specificity for particular areas of the body where drug treatment is required and which have a reduced tendency to self-associate. The present invention thus seeks to provide a solution to the problem of how to fulfill this need by providing targetting portions of pharmaceutically-active conjugates in the form of protein fragments, e.g. generated by the enzymic digestion of adhesive glycoproteins, which have affinity for a specified body tissue involved in a bodily disorder. One advantage of employing these fragments is that it is possible to prepare adhesive glycoprotein fragments which have specificity or at least a high degree of selectivity for single body tissue types, whereas whole adhesive glycoproteins, such as intact fibronectin, usually have a broad range affinity for a number of body tissues. The use of protein fragments therefore makes it possible to prepare conjugates that will bind substantially only to the specified body tissue involved in the disorder being treated. Furthermore, it has been found using fibronectin as an appropriate model, that protein fragments have a reduced tendency to bind under physiological conditions to their parent glycoprotein, which enhances their specificity of binding within the whole body.

According to a first aspect of the present invention, therefore, there is provided a pharmaceutically active conjugate comprising a pharmaceutically active substance for treating a disorder of the body that involves a specified body tissue characterised in that said pharmaceutically active substance is conjugated directly or indirectly with at least one fragment of an adhesive glycoprotein having improved binding specificity compared with the parent protein for the said body tissue.

The glycoprotein will normally possess binding sites specific to at least two different tissues.

Protein fragments suitable for a conjugate according to the present invention may be derived for example by protease digestion of a naturally-occurring adhesive glycoprotein or portion thereof, in glycosylated or non-glycosylated form, or from a genetically engineered equivalent thereof having the same amino acid sequence or the same amino acid sequence apart from one or more changes which do not affect binding specificity. Moreover, it will be appreciated that suitable protein fragments for a conjugate of the present invention may alternatively be prepared directly by recombinant DNA technology or chemical synthesis. The pharmaceutically active substance will preferably be covalently conjugated to the chosen protein fragment or fragments directly or indirectly through a cross-linking reagent or via a carrier molecule which may carry a number of molecules of an active substance as well as one or more fragments of an adhesive protein.

A pharmaceutically active conjugate of this type can be administered by normal means (usually orally or intraveneously), and yet is more readily and efficiently targetted on to particular sites of the body which are involved in a specified bodily disorder. Such a conjugate will tend to bind with a high degree of selectivity to a site of interest readily and rapidly as it is carried past the site within the blood stream or another body fluid and so the tendency for competing side reactions to occur between the active substance in the conjugate and other body tissues will be reduced. This has the dual advantage of decreasing the dosage requirements for treating a specified disorder whilst at the same time reducing the extent of undesirable side effects that are frequently associated with the administration of large quantities of inefficiently-utilised pharmaceutically active substances to the body.

Adhesive glycoproteins and certain digestion fragments thereof are known to have a strong affinity for certain proteins produced by the body. Preferred conjugates of the present invention are therefore of a type that are effective for treating disorders of the body involving an accumulation of tissue containing or consisting of protein matter. In this case, the pharmaceutically active substance may preferably comprise an agent for bringing about the proteolytic degradation of the accumulated protein. Where the accumulated protein consists of a fibrin-based clot, a suitable conjugate of the present invention will comprise a plasminogen activator, for example t-PA, streptokinase (SK) or urokinase (UK), conjugated to a protein fragment with a high degree of selectivity for binding to fibrin, preferably a fibronectin fragment with binding affinity for fibrin, but which unlike whole fibronectin substantially lacks gelatin or collagen binding affinity. Indeed, conjugates of the present invention have been found to be particularly effective when the pharmaceutically active substance is in the form of a protein or enzyme because these can be readily conjugated through covalent bonding to glycoprotein fragments.

Further examples of preferred conjugates according to the present invention are anti-rheumatic drug-protein conjugates suitable for selectively targetting the chosen drug to articular tissue in joints affected by rheumatoid arthritis. This condition is characterised by chronic synovial inflammation leading to release and activation of collagenase with the result that collagen in the connective tissue of affected joints is broken down and denatured to form gelatin. Thus, a conjugate of the present invention for treatment of rheumatoid arthritis will comprise an anti-rheumatic drug such as gold, a gold compound or penicillamine, bound directly or indirectly to one or more protein fragments with a high degree of selectivity for gelatin-binding in the body. As hereinbefore indicated, fibronectin has a gelatin-binding domain and moreover has a higher affinity for gelatin (denatured collagen) than native collagen. Consequently, it is most preferred to employ as the protein fragment component of an anti-rheumatic drug conjugate of the present invention one or more fibronectin fragments comprising a gelatin-binding domain, but having substantially no fibrin-binding affinity.

Other pharmaceutically active substances which may be conjugated with protein fragments to form a conjugate of the present invention are anti-tumour agents, anti-inflammatory agents and anti-bacterial agents which are in the main antibiotics. Examples of substances which can be conjugated are given in EP-A No. 2-0114685 and U.S. Pat. No. 4,587,122 and include daunomycin, mitomycin, cephalothin, penicillin G and secretin. Yet further examples of pharmaceutically active substances which may be conjugated with protein fragments to form conjugates according to the present invention are protein growth factors to promote, for example, localised wound repair and antibodies (e.g. of the IgM or IgG class).

The one essential characteristic which is possessed by pharmaceutically active substances suitable for incorporation within conjugates of the present invention is their ability to combine with proteins, especially adhesive glycoprotein fragments, or non-toxic carrier molecules such as dextran either directly or via a linking group. They may, for example, contain a functional group such as an amino, carboxy or hydroxyl group. One particular active substance of interest for incorporation in conjugates of the present invention is gold, which can be conjugated directly with sulphydryl groups present in proteins.

In order to increase the efficiency of delivery of a pharmaceutically active substance to a specified body tissue, a conjugate of the present invention may be prepared in which the active substance is loaded on to a non-toxic carrier molecule such as a dextran, preferably a protein such as fibronectin or albumin or a portion thereof, and conjugated directly or indirectly with one or more targetting protein fragments. The carrier will generally be covalently conjugated. Clearly, many adhesive protein fragments, for example from 1 to 20, especially from 1 to 5, may be conjugated to a single carrier molecule.

Thus, it will be appreciated that where the chosen carrier is fibronectin or a high molecular weight portion thereof having a range of different binding specificities, these will be largely negated by the attachment of the active substance and protein fragments and will thus be prevented from substantially reducing the selectivity of the conjugate. Use of such a carrier is especially preferred for the preparation of anti-rheumatic conjugates of the present invention wherein gold or a gold compound is employed together with one or more gelatin-binding fibronectin fragments. Conventional administration of a toxic gold compound for treatment of rheumatoid arthritis has the disadvantage that undesirable side effects are liable to occur, particularly as a result of accumulation of gold in the liver and kidneys. However, by employing an anti-rheumatic conjugate of the present invention wherein gold or a gold compound is bound to both a carrier molecule and at least one targetting fibronectin fragment having a high degree of selectivity for gelatin binding in the body, a high concentration of gold can be achieved at arthritic joints with a substantially reduced risk of liver or kidney damage. Particularly preferred are conjugates of this type wherein gold per se, derived for example from aurothiomalic acid or a salt thereof, is directly conjugated to sulphydryl groups of a carrier protein. In such a conjugate, the targetting protein fragment(s), preferably one or more fibronectin fragments having gelatin-binding affinity, but substantially lacking fibrin-binding affinity, will be conjugated to the carrier by means of a cross-linking agent, e.g. cyanamide. Because of its high capacity for binding gold via sulphydryl groups, fibronectin or a portion thereof is especially preferred as the carrier molecule for a conjugate of this type. During preparation of such an anti-rheumatic conjugate employing whole fibronectin or a portion thereof having a gelatin binding domain, precautionary measures may be taken to protect the gelatin-binding affinity of the carrier protein of the final conjugate Thus, direct covalent conjugation of the carrier protein with gold may be carried out in the presence of gelatin, e.g. soluble gelatin or gelatin bound to an agarose-based support such as Sepharose*. Moreover, binding of the targetting protein fragment(s) may be carried out under mild conditions which do not destroy the gelatin-binding ability of the carrier protein. By taking such protective measures to ensure retention of a gelatin binding site in the carrier protein, the selectivity of the final conjugate will not be reduced and indeed it may be enhanced. $\neq$* trade mark The preparation of fragments of an adhesive glycoprotein having enhanced specificity compared with the parent protein for a single tissue type can be achieved by adopting the following procedural steps:

(a) Select an adhesive glycoprotein having the desired tissue binding specificity;
(b) Fragment the selected protein, preferably by enzymic digestion with a protease, e.g. trypsin, thrombin or cathepsin D; and
(c) Select those fragments which have specific affinity or at least a high degree of selectivity compared with the parent protein for the body tissue involved in the disorder to be treated.

In the case of preparation of a conjugate of the present invention wherein the pharmaceutically active substance is non-proteinaceous, e.g. gold or a gold compound, it will be understood that the active substance may be conjugated directly or via a cross-linking reagent to the adhesive protein selected in step (a) prior to proteolysis, the conjugation conditions being chosen so that the adhesive protein retains binding affinity for the tissue of interest.

Step (c) is preferably conducted by affinity chromatography. Thus, the protein fragments resulting from proteolysis in step (b) may be subjected to affinity chromatography on an affinity support having specific binding affinity for the tissue binding site of interest or a closely associated non-tissue binding site. The bound fragments may then be eluted and, if necessary, one or more further affinity chromatography steps subsequently carried out to remove fragments which carry in addition to the tissue binding site of interest one or more additional tissue binding sites. The initial affinity chromatography step and any subsequent affinity chromatography steps may, for example, be carried out on an affinity support having immobilized thereon appropriate body tissue or simulated body tissue. For such an affinity support, the tissue or simulated tissue may be conveniently immobilized on an agarose-based support, e.g. Sepharose.

Where the chosen protein for proteolysis has more than one tissue binding specificity, alternatively in order to obtain fragments having the desired enhanced specificity for a particular tissue type, step (c) may begin with subjecting the protein fragments from step (b) to one or more separation steps in which protein fragments having affinity for body tissues other than the tissue of interest are selectively removed. Each such separation step may be conveniently performed, for example, by affinity chromatography on immobilised body tissue (or simulated body tissue) for which binding affinity is not required in the fragments of interest. Finally, the desired fragments may be isolated by affinity chromatography employing a further affinity support with immobilised body tissue or simulated body tissue having affinity for the tissue binding site of interest or by employing an affinity support with specific binding affinity for a non-tissue binding site closely associated with the required tissue binding site.

The size of the selected fragments will depend upon the size of the protein from which the fragments are generated, the method of protein fragmentation (which is preferably by proteolytic enzyme digestion), and on the extent and severity of the fragmentation method employed.

One protein from which the fragments can be derived is the naturally-occurring adhesive glycoprotein fibronectin (m.w. 440,000), which is known to possess a wide range of binding sites, including binding sites for gelatin and fibrin, and can be readily digested into fragments by proteolytic enzymes. It is found in plasma and other body fluids and is associated with connective tissues, cell surfaces and basement membranes. Its wide variety of biological functions is attributed to a series of specific binding sites which bind it not only to gelatin and fibrin, but also to cell surfaces, glycosaminoglycans and other macromoleculaes. Plasma fibronectin is composed of two very similar, but non-identical polypeptide chains which are connected by a disulphide bond at the COOH-terminus and is more susceptible to proteolysis than other basement membrane and plasma proteins. Serine proteases cleave intact fibronectin initially at two preferential sites, releasing a short COOH-terminal fragment containing the interchain disulphides and an NH$_2$-terminal fragment, mw 27,000-30,000. This carries binding sites for fibrin, actin, S. aureus and heparin and a cross-linking site for plasma transglutaminase (factor XIIIa). The digestion proceeds yielding the binding domains shown below:

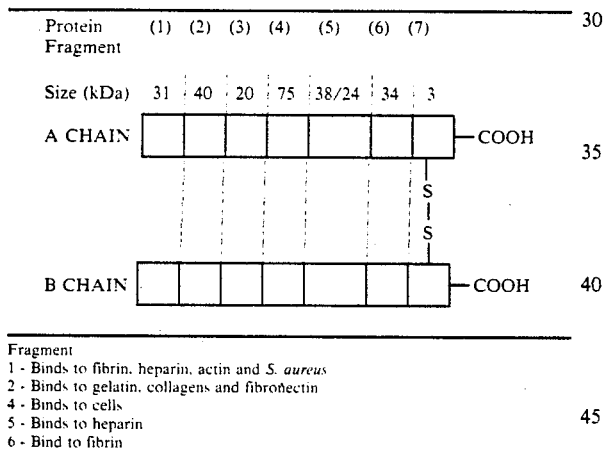

Fragment
1 - Binds to fibrin, heparin, actin and S. aureus
2 - Binds to gelatin, collagens and fibronectin
4 - Binds to cells
5 - Binds to heparin
6 - Bind to fibrin Fibronectin fragments having binding affinity for fibrin in the absence of gelatin-binding affinity or gelatin-binding affinity in the absence of fibrin-binding affinity may be conveniently isolated from a mixture of fibronectin fragments, e.g. a protease digestion mixture of whole fibronectin, by an appropriate two stage affinity chromatography procedure employing a fibrin monomer-affinity support, e.g. fibrin monomer-Sepharose, and a gelatin-affinity support e.g. gelatin-Sepharose. Since the fibrin-binding sites of fibronectin are closely associated with heparin-binding sites, the fibrin monomer-affinity support in the above-indicated fragment purification procedures may be advantageously substituted by a heparin-affinity support, e.g. heparin-Sepharose, which has a higher capacity than fibrin monomer-sepharose and can be more readily prepared. Indeed, heparin-Sepharose may be obtained from commercial sources, e.g. Pharmacia A.B.

The preferred molecular weight range of fibronectin fragments having fibrin binding specificity is from 25 to 400 kDa as measured by HPLC (high performance liquid chromatography) or from 25 to 200 kDa as measured by SDS-PAGE (sodium dodecyl sulphate polyacrylamide gel electrophoresis), whereas the molecular weight range of fibronectin fragments which have gelatin binding specificity is preferably in the range 40 to 500 kDa as measured by HPLC or 40 to 200 kDa as measured by SDS-PAGE, the smaller fragments in these ranges having increased specificity. The higher molecular weights recorded when using HPLC are probably due to association of fragments before or during measurement which give rise to an increase in apparent molecular weights.

Thus, according to a further aspect of the present invention, we provide a method of preparing a pharmaceutically active conjugate of the present invention which comprises conjugating a pharmaceutically active substance directly or indirectly to at least one fragment of an adhesive glycoprotein having improved binding specificity for a body tissue involved in the disorder to be treated compared with the whole adhesive protein or, where the pharmaceutically active substance is not a protein, conjugating the pharmaceutically active substance to the whole adhesive glycoprotein or a portion thereof, optionally with protection of binding sites specific to the said body tissue, followed by proteolysis to produce protein fragments carrying conjugated pharmaceutically active substance and selection of at least one of said fragments having improved binding specificity compared with the said protein or portion thereof.

Thus, for example, an anti-rheumatic conjugate according to the present invention may be prepared by directly conjugating gold to sulphydryl groups of an adhesive protein possessing gelatin-binding affinity, e.g. whole fibronectin, followed by protease digestion and selection of a conjugate with improved selectivity over the parent conjugate for gelatin-binding in the body. Where fibronectin or a gelatin-binding portion thereof is chosen as the starting adhesive protein, gold conjugation will be carried out in the presence of gelatin, e.g. soluble gelatin or gelatin-bound to an agarose-based support, so as to protect the gelatin-binding site of the adhesive protein.

In the case of a process according to the present invention where one or more fragments of an adhesive protein having improved binding specificity compared with the parent protein for the tissue of interest are employed for conjugation to a pharmaceutically active substance, the pharmaceutically active substance may be bound, preferably covalently, to a carrier prior to conjugation directly or indirectly with the targetting protein fragment(s) or such carrier binding may be carried out subsequent to protein fragment binding, in which case conditions will be chosen so that the required tissue binding capability of the protein fragment(s) is retained. Where a conjugate of the present invention comprising as the pharmaceutically active substance a non-proteinaceous species is generated by protease digestion of a larger adhesive protein-containing conjugate, it may also be feasible to subsequently bind the selected conjugate to a carrier without substantially reducing the desired tissue binding specificity.

The activity of conjugates of the present invention increases with increasing loading of active substance bound to the protein fragment(s) and so the active substance is preferably present in molar excess within the conjugate. However, too high a loading of active substance will tend to mask the required tissue binding site on the tissue-binding substrate and may give rise to poor conjugation efficiency. For this reason, a conjugate of the present invention preferably contains from 1 to 100, more preferably from 1 to 50, moles of active substance (usually a single compound or element) per mole of protein fragment. When the active substance consists of a protein or enzyme or other high molecular weight substance, the molar ratio of protein fragment to active substance in the conjugate is preferably from 1:1 to 1:10. On the other hand, active substances of low molecular weight, for example gold atoms, are preferably present at higher loading ratios, for example 1:10 to 1:50.

In the preparation of a conjugate according to the present invention, other than a gold-protein fragment anti-rheumatic conjugate as hereinbefore described, the protein fragment or fragments are most preferably bound with the pharmaceutically active substance using a known protein cross-linking agent such as a carbodiimide, a dialdehydo derivative of a dicarboxyliic acid, a diisocyanate, or an oxidised dextran having an aldohexopyranose ring-cleaved structure.

Suitable carbodiimides include any of those disclosed in U.S. Pat. No 4,046,871 and may be selected from any of the following:

1-ethyl-3-(3-dimethyl-aminopropyl)-carbodiimide hydrochloride,
1-cyclohexyl-3-(2-morpholinoethyl)-carbodiimide metho-p-toluene-sulphonate,
1-cyclohexyl-3-(4-diethylaminocyclohexyl) carbodiimide metho-p toluene-sulphonate,
1-cyclohexyl-3-($\beta$-diethylamino-ethyl)-carbodiimide,
1-ethyl-3-(2-morpholino-ethyl)-carbodiimide hydrochloride,
1-ethyl-3-(2-morpholino-ethyl)-carbodiimide sulfate and cyanamide.

Where the cross-linking agent employed consists of a dialdehydo derivative of a dicarboxylic acid, the acid is preferably a carboxy-terminated $C_2-C_5$ straight chain alkane and is most preferably glutaric acid, the dialdehydo derivative of which is glutaraldehyde. A suitable method of conjugation employing glutaraldehyde is given by J. W. Payne in *Biochem J* (1973) 135, 867–873.

An example of a suitable diisocyanate is hexamethylene diisocyanate.

Suitable oxidised dextrans and methods of conjugation employing the same are disclosed in U.S. Pat. No. 4,587,122.

Covalent coupling of a pharmaceutically active substance with one or more protein fragments for preparation of a conjugate of the present invention may, for example, be carried out by (a) mixing and reacting simultaneously the protein fragment(s), cross-linking agent and pharmaceutically active substance, (b) reacting the cross-linking agent with the pharmaceutically-active substance, and then reacting the product with the protein fragment(s), or (c) reacting the cross-linking agent with the protein fragment(s), and then reacting the product with the pharmaceutically active substance.

Covalent coupling of a pharmaceutically active substance with one or more protein fragments to form a conjugate of the present invention will generally be conducted in an aqueous solution of pH 5 to 9, preferably 6 to 8, and preferably in a buffer solution. Preferred reaction temperatures are 10° C. to 30° C., particularly room temperature. The reaction time is preferably from 0.5 to 15 hours, more preferably from 0.5 to 5 hours. The preferred molar ratio of pharmaceutically active substance to protein fragment in the reaction mixture is preferably from 1:1 to 100:1, with, if appropriate, sufficient or excess cross-linking agent being present to effect conjugation of the two.

Active substance-protein fragment conjugates produced by the methods described above are preferably separated from the reaction mixture in which they are produced by affinity chromatography on immobilised body tissue or simulated body tissue for which the protein fragments have affinity.

Subsequent covalent coupling of an active substance protein fragment conjugate to a high molecular weight carrier, e.g. fibronectin, albumin or a high molecular weight portion thereof, may also, for example, be carried out by employing a cross-linking reagent under mild conditions as specified above. Preferably, however, when it is desired to prepare a conjugate according to the present invention with a carrier, the carrier will be covalently coupled to the pharmaceutically active substance, either directly or via a coupling reagent, prior to protein fragment binding. Thus, for preparation of a preferred anti-rheumatic conjugate of the present invention wherein gold is conjugated to a carrier protein, an appropriate gold compound, e.g. aurothiomalic acid or a salt thereof such as sodium aurothiomalate, will preferably initially be reacted with the sulphydryl groups of the carrier so as to directly couple gold via these groups. As hereinbefore indicated, where the protein chosen for this step is fibronectin or a gelatin binding portion thereof, the carrier conjugation may be carried out in the presence of gelatin, e.g. soluble gelatin or gelatin bound to an agarose based support, e.g. Sepharose, in which case the carrier protein will retain a gelatin-binding site. Alternatively, fibronectin may, for example, conveniently be directly coupled with gold when conjugated itself to an agarose-based support such as Sepharose or when adsorbed on to fibronectin thus bound. For the preparation of a carrier containing, anti-rheumatic conjugate of the present invention, gold may also conveniently be directly conjugated to albumin via sulphydryl groups of the protein by, for example, reacting an appropriate gold compound such as sodium aurothiomalate with albumin bound to an agarose-based support, e.g. an albumin-Sepharose column. If in the preparation of an anti-rheumatic conjugate of the present invention gold is initially conjugated to a protein which is itself covalently conjugated on a support, e.g. Sepharose, it will be understood that the required gold-carrier protein conjugate may be released by appropriate protease digestion, i.e. the carrier protein of the final conjugate will be derived from a larger pre-carrier protein.

According to a third aspect of the present invention, there is provided a pharmaceutical composition which comprises a pharmaceutically active conjugate according to the first aspect dissolved or dispersed in a pharmaceutically acceptable diluent or carrier, for example saline solution. Administration of the composition may be by intravenous injection or by oral ingestion of the composition in the form of a tablet or ingestible .liquid. A typical dose of aqueous composition may contain 10–300 mg of conjugate in 0.05–10 ml of composition.

According to a further aspect of the present invention, we provide a conjugate according to the present invention for use in therapeutic treatment of a human or non-human animal, e.g. conjugates of the present invention wherein a plasminogen activator is bound to a fibronectin fragment having predominantly fibrin targetting capability for use in treatment of a thrombotic condition or use of a conjugate according to the present invention wherein an anti-rheumatic substance, e.g. gold, is conjugated to a fibronectin fragment having predominantly gelatin targetting capability for use in the treatment of rheumatoid arthritis.

We also provide as a still further aspect of the present invention, use of a conjugate according to the present invention for the preparation of a composition for use in the treatment of a disorder involving a specified body tissue for which said conjugate has predominant targetting capability.

As yet another aspect of the present invention, we additionally provide a method of delivery of a pharmaceutically active substance to a tissue involved in a disorder of the body wherein said pharmaceutically active substance is administered in the form of a conjugate according to the present invention having predominant targetting capability for said tissue.

The following non-limiting examples are intended to illustrate the present invention.

EXAMPLE 1

PREPARATION OF ANTI-THROMBOTIC CONJUGATES

A. Materials

Figure 1:
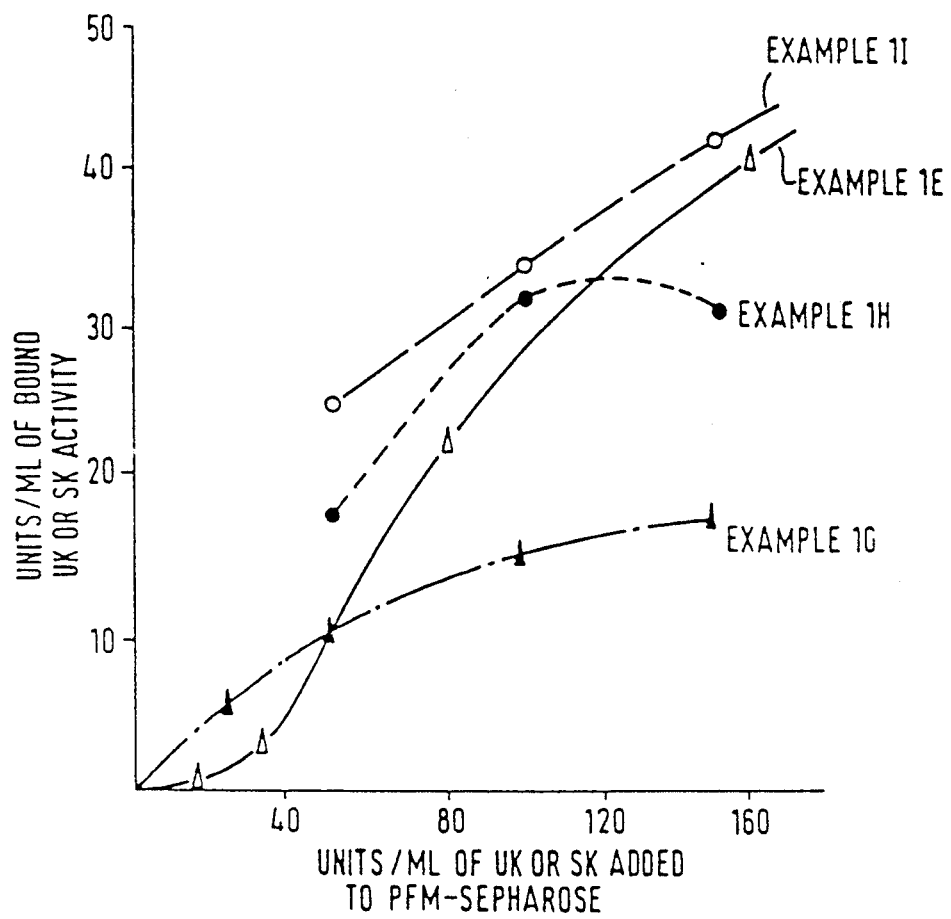
FIG. 1 shows the correlation between the amount of conjugate added to the immobilized physiological fibrin monomer (PFM) and the amount of plasminogen activator (PA) subsequently bound to it.

A1. Preparation of Physiological Fibrin Monomer (PFM)

The PFM used in the following examples consisted of fibrinogen which was purified by precipitation from blood plasma cryoprecipitate supplied by the Plasma Fractionation Laboratory, Churchill Hospital, Oxford, England (GB). This PFM contained 68 wt.% fibrinogen, 10% fibronectin (a natural contaminant) with traces of factor VIII:RAg and factor XIIIa. Since normal fibrin blood clots invariably incorporate fibronectin, this PFM was subsequently used as a simulated fibrin blood clot.

A2. Preparation of Fibronectin-Free Fibrin Monomer (FFFM)

FFFM was prepared by removing fibronectin from the fibrinogen within PFM by subjecting the fibrinogen to gelatin-sepharose affinity chromatography. The preparation of columns used in this chromatographic procedure is described below.

B. General Procedures

B1. Preparation and Use of Gelatin-Sepharose Affinity Chromatography Columns

Gelatin-Sepharose columns were prepared following the coupling procedure outlined in the manufacturer's (Pharmacia, Uppsala. Sweden) recommended procedure for adsorbing materials on to CNBr-activated Sepharose 4B. A coupling ratio of 15 mg gelatin per g moist weight Sepharose gel was used to prepare the columns.

The running conditions for the prepared columns were adapted from Vuento and Vaheri, *J. Biochem* (1979) 183, p.331 with the following changes:-the running buffer consisted of a 10 mM phosphate, 10 mM citrate, 150 mM NaCl solution pH 7.5 and elution was achieved with 1 M arginine in phosphate buffered saline. The columns were used at 4° C.

B2. Preparation and Use of Fibrin Monomer-Sepharose Affinity Chromatography Columns Fibrin monomer columns were prepared following the method of Heene and Matthias, *Throm. Res.* (1973) 2, p.137. Two types of column were prepared, in which the monomer used was either Physiological Fibrin Monomer (PFM) or Fibronectin Free Fibrin Monomer (FFFM). PFM—Sepharose and FFFM—Sepharose columns were prepared by coupling either PFM or FFFM to CNBr-activated Sepharose 4B by the manufacturer's (Pharmacia) recommended procedure. The running conditions for both types of column were the same as those used in General Procedure B1 described above.

B3. Preparation and use of Heparin-Sepharose Affinity Chromatography Columns

Heparin-Sepharose columns were prepared following the procedure recommended by the manufacturer for coupling materials on to CNBr-activated Sepharose 4B. Such columns are also available 'ready-coupled' from the same manufacturer (Pharmacia, Uppsala, Sweden). Running conditions were as described above for gelatin-Sepharose, except that the running buffer consisted of a 10 mM phosphate, 20 mM NaCl, 0.5 mM EDTA solution, pH 7.5 and elution was achieved using a 10 mM phosphate, 0.5 M NaCl, 0.5 mM EDTA solution, pH 7.5. Columns were used at room temperature.

B4. Separation of Protein Fragments on Sephacryl*S200

Further resolution of protein fragments selected by affinity chromatography was carried out by gel permeation chromatography using Sephacryl S200. The running buffer was 10 mM phosphate, 150 mM NaCl, pH 7.5. Approximately 10 mg were applied to a 320 ml bed volume column (2.2×84 cm) at a flow rate of 12 ml/hr.
≠* trade mark B5. Assay for Plasminogen Activators The concentrations of plasminogen activator in solutions were determined using the Kabi Diagnostica "Initial Rate of Reaction" method for the Determination of Plasminogen in Plasma, using S-2251 chromogenic substrate (Kabi Vitrium, Sweden). The protocol for this method is summarised below:

(1) Dilute human blood plasma with assay buffer solution consisting of 50 mM Tris-HCl, pH 7.4 containing 12 mM NaCl in the volumetric ratio of plasma to buffer solution of 1:20 and add 200 microliters of the diluted plasma to a reaction tube.

(2) Incubate the tube at 37° C. for 2 to 6 minutes.

(3) Add either a known number of units (e.g. 10 or 25 units) of plasminogen activator or a test conjugate containing plasminogen activator, made up to 100 microliters with assay buffer solution, to the tube.
(4) Incubate the tube at 37° C. for 10 minutes.
(5) Add 700 microliters of substrate solution consisting of S-2251 diluted to 0.86 mM working solution with assay buffer.
(6) Mix, transfer the contents of the tube to a microcuvette and measure the change with time of the absorbance (A) of the mixture at 37° C. to 405 nm wavelength light ($\Delta A_{405}$).
(7) Calculate $\Delta A_{405}$ per minute and plot this result against the units of plasminogen activator per ml present in the buffer solution.

An alternative plasminogen activator assay was used to test for such activity on PFM - Sepharose. An endpoint assay had to be used because Sepharose could not be tested by the "initial rate of reaction" assay described above. The assay protocol is summarised below:
(1) Partly dry the test PFM - Sepharose by suction filtration on a sinter funnel.
(2) Weigh 100mg of test PFM - Sepharose (moist weight) into a reaction tube.
(3) Add 200 microliters of diluted human blood plasma.
(4) Mix
(5) Incubate the tube for 10 minutes at 37° C.
(6) Add 700 microliters of S-2251 chromogenic substrate (Kabi) solution at 37° C., mix and incubate for exactly 180 seconds.
(7) Add 100 microliters of 50% acetic acid and mix immediately to stop the reaction.
(8) Measure the absorbance of the resulting solution to 405 nm within 4 hours and relate the result to a standard curve for known concentrations of plasminogen activator against absorbance.

C. Generation Of Protein Fragments By Digestion Of An Adhesive Protein With Proteolytic Enzymes Fibronectin was chosen as the starting adhesive protein. Prior to digestion, the fibronectin was checked for purity by size exclusion High Performance Liquid Chromatography (HPLC) using an Ultropac TSK G 4000 SW column, fractionation range from 1000kDa down to 5kDa. This was necessary in order to standardise the fibronectin fragments generated by proteolytic enzyme digestion, since the presence of fibronectin aggregates or fragments in the fibronectin prior to digestion could have affected the subsequent digestion process.

C1. Digestion of fibronectin with trypsin 10 mg of fibronectin in 10 ml of PBS (PBS =phosphate buffered saline pH 7.5 containing 10 mM sodium phosphate and 0.15 M NaCl) was digested with 0.05 mg of trypsin for 2 hours at 37° C. Trypsin is an endopeptidase capable of specifically cleaving peptide bonds adjacent to an arginine or lysine residue. Samples of the reaction mixture were removed at the times stated in Table 1 below. The reaction was stopped after 2 hrs by the addition of 0.1 mg of soya bean inhibitor.

The molecular weights of the fibronectin fragments produced by digestion were determined by gel permeation high performance liquid chromatography (HPLC) analysis using a TSK G 3000 SW column. The running buffer was a 0.1 M phosphate solution pH 6.8 containing 0.05% sodium azide, flow rate 0.4 ml/min, with a 70 minute elution time. The absorbance of the eluate was monitored at 280 nm for the presence of fibronectin fragments.

TABLE 1

| Digestion of Fibronectin with Trypsin | | | | | | |
|---|---|---|---|---|---|---|
| Incubation time (minutes) | Protein Fragment Molecular Weight (kDa) | | | | | |
| 0   | 439 | —   | —   | —   | —  | —  |
| 10  | —   | 358 | —   | 140 | 56 | 42 |
| 30  | —   | 358 | 181 | 140 | 56 | 42 |
| 60  | —   | 358 | 181 | 140 | 56 | 42 |
| 120 | —   | —   | 181 | 140 | 56 | 42 |

Extensive digestion of fibronectin by trypsin (that is, for more than 10 minutes) dramatically reduced its gelatin binding activity, as measured by a competitive, enzyme-linked assay (Doran et al, *Vox Sang* (1983) 45, 243–251). Consequently, the principal of using the minimum effective digestion time of 10 minutes was adopted.

C2. Digestion of fibronectin with thrombin

The procedure of C1 was repeated, except that the fibronectin was digested with 250 international units (iu) of thrombin instead of trypsin. Thrombin is a serine protease responsible for the final conversion of fibrinogen to fibrin during blood clot formation. The digestion was stopped after 120 minutes by the addition of benzamidine to a final concentration of 8mM in the reaction mixture. Samples of the reaction mixture were removed at the times stated in Table 2 below and were analysed using the same procedure as outlined in C1.

TABLE 2

| Digestion of Fibronectin with Thrombin | | | | | | |
|---|---|---|---|---|---|---|
| Incubation time (minutes) | Protein Fragment Molecular Weight (kDa) | | | | | |
| 0   | 439 | —   | —   | —   | —  | —  |
| 10  | 468 | 218 | 83  | —   | —  | —  |
| 30  | 462 | 218 | 83  | —   | —  | —  |
| 60  | 468 | —   | 83  | 50  | 27 | 23 |
| 120 | 470 | 218 | 110 | 45  | 28 | —  |

D. Selection and Purification of Protein Fragments

Products of fibronectin digestion with trypsin or thrombin comprising a mixture of fragments with either or both gelatin-binding affinity and fibrin-binding affinity or neither of these two binding specificities were used as the starting material to select out fibronectin fragments having fibrin-binding affinity in the absence of gelatin-binding affinity or vice versa using a dual column affinity chromatography procedure.

D1. Use of thrombin generated fibronectin fragments

The method of C2 was repeated on a larger scale with the quantities of reagents and solution volume increased proportionally. The product, consisting of a solution of fibronectin fragments obtained by fibronectin digestion for 120 minutes at 37° C. with thrombin, was divided into several aliquots containing known amounts of fibronectin fragments. These aliquots were applied directly to a 15 ml column of gelatin-Sepharose (see the general procedure B1 described above) in order to remove those protein fragments with an affinity for gelatin possessing both gelatin and fibrin-binding sites or a gelatin binding site in the absence of a fibrin-binding site. The unbound fractions of these aliquots, which contained protein fragments with an affinity for fibrin in the absence of gelatin-binding affinity and protein fragments having neither fibrin nor gelatin-binding affinity, were then applied to a 15 ml column of FFFM-Sepharose (see the general procedure B2 described above). The eluates from the FFFM-Sepharose column contained purified protein fragments with binding affinity for fibrin but no binding affinity for gelatin. The results of this two-stage affinity-chromatography procedure are given in Table 3 below in terms of product yields.

ously described in B3 above. Bound fractions which contained protein fragments with an affinity for heparin and fibrin were then applied to a 30 ml column of gelatin-Sepharose by the procedure described in B1 Unbound fractions contained purified protein fragments with an affinity for heparin/fibrin. Those binding to gelatin-Sepharose, which were those with both gelatin and heparin/fibrin binding activity, were discarded.

TABLE 3

2-stage affinity chromatography of fibrin-binding protein fragments

| Sample Applied (mg) | Gelatin-Sepharose Affinity Chromatography | | % Protein Recovery | FFFM-Sepharose Affinity Chromatography | | % Protein Recovery |
|---|---|---|---|---|---|---|
| | mg bound | mg unbound | | mg bound | mg unbound | |
| 33.0 | 2.84 | 22.94 | 78 | 1.19 | 3.79 | 11.5 |
| 15.0 | 6.4 | 6.5 | 86 | 1.72 | 2.44 | 68.4 |
| 7.2 | 2.64 | 2.56 | 72 | 0.74 | 1.40 | 81.0 |

The recoveries of protein fragments at each stage given in Table 3 above were based on the absorbance of fractions at 280 nm using the extinction coefficient for fibronectin $$(E_{280}^{1cm} \; 1 \; mg/ml = 1.28).$$

The eluates from the FFFM-Sepharose and gelatin-sepharose columns were analysed by HPLC to determine the molecular weights of both gelatin binding and fibrin binding fragments. The sizes of fragments eluted from the gelatin column were found to be 435 and 296 kDa. The sizes of the fragments eluted from the FFFM column were found to be 382, 110 and 45 kDa.

It will be understood that the above 2-stage affinity chromatography procedure can be reversed (FFFM-adsorption followed by gelatin adsorption) to afford eluates from the second adsorption stage that contain purified protein fragments with binding affinity for gelatin in the absence of fibrin binding affinity.

D2. Use of Trypsin generated fibronectin fragments (a) The procedure of D1 was repeated using fibronectin digested for 10 minutes with trypsin in a larger scale version of the procedure described in C1 above. The eluates from the affinity columns were analysed by HPLC. This revealed that protein fragments were eluted from the gelatin column of sizes 358, 140, 119 and 69 kDa and protein fragments of 56 kDa were eluted from the FFFM column.

(b) The close association between the fibrin binding sites and heparin binding sites in fibronectin was exploited by using heparin-Sepharose instead of FFFM-Sepharose in an alternative dual column affinity chromatography procedure to isolate fibronectin fragments having fibrin-binding affinity in the absence of gelatin-binding affinity.

A solution of tryptic fragments of fibronectin was prepared as in D2(a) above and the solution divided into several aliquots containing known amounts of fibronectin fragments. Aliquots were applied to a 15 ml column of heparin-Sepharose by the general procedure previously described in B3 above.

Results of this two stage affinity chromatography procedure are given in Table 4 below.

The eluates from the adsorbent columns were analysed by HPLC. This revealed that the sizes of the protein fragments from the two-stage purification procedure were 360, 181, 140 (minor), 56 and 42 kDa.

While all of these fragments retained heparin/fibrin binding activity and did not bind to gelatin, the different fragment sizes generated by this method could be further resolved by separation on Sephacryl S200 as described in B4 above. The proportions of the fragments in the heparin binding, non-gelatin binding fraction are given in Table 5.

The proportion of protein fragments at each stage which were fibrin-binding was determined by applying aliquots to a PFM-Sepharose column by the procedure of B2 above.

TABLE 4

| Sample Applied (mg) | Heparin-Sepharose affinity chromatography | | % Protein Recovery | Gelatin-Sepharose Affinity Chromatography | | % Protein Recovery |
|---|---|---|---|---|---|---|
| | mg bound | mg unbound | | mg bound | mg unbound | |
| 23.7 | 11.2 | 13.7 | 105.0 | 1.8 | 9.1 | 97.3 |
| 6.0 | 3.22 | 2.72 | 99.0 | 0.32 | 2.85 | 98.4 |

TABLE 5

| Purification Stage | Recovered Protein (mg) | % Starting material | % Fibrin-binding activity |
|---|---|---|---|
| Fibronectin trypsin digest | 23.7 | 100 | 23 |
| Heparin-Sepharose (bound fractions) | 11.12 | 45.6 | |
| Gelatin-Sepharose (unbound fraction) | 9.10 | 37.3 | 63 |
| Sephacryl S200 Fractions: | | | |
| 360K | 2.61 | 11.0 | 23 |
| 181K | 1.49 | 6.3 | 39 |
| (140K - minor peak) | N.D. | N.D. | |
| 56K | 1.75 | 7.4 | 68 |
| 42K | 1.19 | 5.0 | |

N.D. — Not determined

It will be appreciated that if the two types of affinity chromatography column are used in opposite order, i.e. the bound fraction of a gelatin-Sepharose column is applied to a heparin-Sepharose column, this will result in isolation of fibronectin fragments having gelatin-binding affinity in the absence of fibrin and heparin binding affinity.

E. Conjugation of selected fibronectin fragments having fibrin-binding affinity to streptokinase An aqueous solution of a commercial streptokinase preparation (trade name "Kabikinase" supplied by Kabi Vitrum AB Haematology, Stockholm, Sweden) containing by weight 4% streptokinase, 50% albumin, 44% sodium salts and 2% $H_2O$ was passed through a column of Cibacron Blue-Sepharose CL6B adsorption resin at ambient temperatures in order to adsorb the albumin, thereby separating it from the streptokinase. The unbound fractions were assayed for plasminogen activator activity.

2 mls of an aqueous solution of the unbound fractions, containing about 600 units of albumin-depleted streptokinase per ml, were prepared by the procedure described above. An equal volume of an aqueous solution of fibrin-binding fibronectin fragments prepared in accordance with the method of D1 (0.12 mg per ml) was added to the streptokinase solution. The pH of the mixture was adjusted to 7.0 by the addition of a small amount of 0.1 N hydrochloric acid. To the resulting solution was added, with stirring and at ambient temperature, a 0.588 M 1-ethyl-3-(3-dimethylaminopropyl)-carbodiimide hydrochloride solution until the content of the carbodiimide hydrochloride in the resulting solution reached 0.5% (w/v). Stirring was continued for 2 hours to produce a conjugated streptokinase-protein fragment product in the reaction mixture. The desired product was recovered from the mixture by adsorption on to FFFM-Sepharose followed by elution with 0.2M NaCl solution. The concentration of the conjugate in the resulting eluate was, where necessary, increased by pressure ultra-filtration.

The activity of the streptokinase within the conjugate at various conjugate concentrations in solution was measured by the procedure described in B5 above against equivalent concentrations in solution of unconjugated streptokinase. The results of these measurements are given in Table 6 below.

TABLE 6

| SK concentration (units/ml) | Activity ($\Delta A_{405}$ min$^{-1}$) | |
|---|---|---|
| | SK alone | SK-protein fragment conjugate |
| 10 | 0.019 | 0.010 |
| 20 | 0.036 | 0.014 |
| 30 | 0.053 | 0.021 |

These results show that streptokinase activity in the conjugate varied from 38%-52% of that present in its unconjugated form.

F. Conjugation of selected fibronectin fragments having fibrin-binding affinity to urokinase 2240 units of urokinase (UK) were dissolved in 2 ml of pH 7.3 buffer solution (20mM Tris HCl, 0.15 M NaCl) containing 0.12 mg/ml of fibrin-binding fibronectin fragments prepared in accordance with the method of D1. The total content of protein fragments within the solution was equivalent to $3.27 \times 10^{-6}$M. To the resulting solution was added 80 microliters of 5% (w/v) glutaraldehyde solution in water (final concentration 0.2%). The resulting solution was mixed on a vortex mixer while the glutaraldehyde was added. Mixing was continued for 1 minute and the solution was then incubated at room temperature (20° C.) for 24 hours. The desired product was recovered using FFFM-Sepharose as described in procedure E above. The concentration of the conjugate in solution was adjusted as necessary either by pressure ultrafiltration concentration or by dilution with buffer solution.

The activity of the urokinase within the conjugate at various conjugate concentrations in solution was measured by the procedure described in B5 above against equivalent concentrations in solution of unconjugated urokinase. The results of these measurements are given in Table 7.

TABLE 7

| UK concentration (units/ml) | Activity ($\Delta A_{405}$ min$^{-1}$) | |
|---|---|---|
| | UK alone | UK-protein fragment conjugate |
| 10 | 0.020 | 0.006 |
| 20 | 0.0475 | 0.010 |
| 30 | 0.0575 | 0.013 |

The results given in Table 7 above show that the plasminogen activity of the urokinase within the conjugate is 21%-30% of its activity when in its original, unconjugated form.

G. Alternative method for conjugation of selected fibronectin fragments having fibrin-binding affinity to urokinase 2240 units of UK were dissolved in 2 ml of pH 7.3 buffer solution (20mM Tris-HCl, 0.15M NaCl) containing 0.12 mg/ml ($3.27 \times 10^{-6}$M) of fibrin-binding fibronectin fragments prepared as in D1 above. The pH of the solution was adjusted to 5 by the addition of small amounts of 0.1 N hydrochloric acid. To the resulting solution was added, with stirring and at ambient temperature, a 0.588 M 1-ethyl-3-(3-dimethylaminopropyl)-carbodiimide hydrochloride solution until the content of the carbodiimide hydrochloride in the resulting solution reached 1.0% (w/v). Stirring was continued for 1 hour to produce a conjugated urokinase-fibronectin fragment product in the reaction mixture. A mild form of carbodiimide cross-linking was also suitable using 0.5% (w/v) carbodiimide for 2 hours at pH 7.0 (i.e. no HCl added). The desired conjugated product was recovered from the mixture by adsorption on to FFFM-Sepharose followed by elution with 0.2 M NaCl solution. The concentration of the conjugate in the resulting eluate was, where necessary, increased by pressure ultrafiltration.

The activity of urokinase within the conjugate at various conjugate concentrations in solution was measured as in the procedure F above. The results of these measurements are given in Table 8 below.

TABLE 8

| UK concentration (units/ml) | Activity ($\Delta A_{405}$ min$^{-1}$) | |
|---|---|---|
| | UK alone | UK-protein fragment conjugate |
| 10 | 0.0225 | 0.015 |
| 20 | 0.050 | 0.033 |
| 30 | 0.060 | 0.042 |

It may be seen from Table 8 above that the plasminogen activator activity of the UK within the conjugate varies from 64%-67% of its activity when in its original, unconjugated form.

H. Conjugation of selected fibronectin fragments having fibrin-binding affinity to urokinase as a measure of fibrin-binding fibrinolytic agent in the test conjugates. The results of these determinations are given in Table 9 below.

TABLE 9

| conjugate preparation procedure | Units/ml of PA within conjugate added to immobilised PFM | Units/ml of PA bound to Sepharose | % of PA activity bound to Sepharose | Units of PA reacted per mg of protein fragment |
|---|---|---|---|---|
| E | 16 | 0.42 | 2.6 | 133 |
|   | 32 | 3.2 | 10.0 | 267 |
|   | 80 | 23.0 | 28.0 | 667 |
|   | 160 | 41.6 | 26.0 | 1333 |
| G | 25 | 6.0 | 23.6 | 208 |
|   | 50 | 10.4 | 20.7 | 417 |
|   | 100 | 15.3 | 15.3 | 833 |
|   | 150 | 17.8 | 11.9 | 1250 |
| H | 50 | 18.13 | 36.3 | 833 |
|   | 100 | 32.0 | 32.0 | 1667 |
|   | 150 | 31.6 | 21.1 | 2500 |
| I | 50 | 25.6 | 51.2 | 1667 |
|   | 100 | 34.2 | 34.2 | 3111 |
|   | 150 | 42.9 | 28.6 | 5000 |

The method of G above was repeated except that the concentration of fibrin-binding fibronectin fragments in the Tris-HCl-saline solution was reduced to 0.06 mg/ml.

I. Conjugation of selected fibronectin fragments having fibrin-binding affinity to urokinase The method of G above was repeated except that the concentration of fibrin-binding fibronectin fragments in the Tris-HCl-saline solution was reduced to 0.03 mg/ml.

J. Binding plasminogen activator-protein fragment conjugates to simulated blood clot tissue (fibrin Monomer)

In order to test the efficiency of the conjugates prepared by the procedures described in E and G–I above, solutions of each conjugate were contacted with immobilised simulated blood clot tissue and the amount of plasminogen activator adsorbed by the tissue was measured. It is known that there is a direct correlation within the body between the uptake of plasminogen activator by fibrin clots and their rate of subsequent fibrinolysis and so this test provides a useful indication of the pharmacological value of these conjugates.

The simulated tissue selected was physiological fibrin monomer (PFM) preparation which is known to include many of the components of a normal blood clot. Crude fibrin monomer (Kabi Diagnostica), herein referred to as PFM, was immobilised on to Sepharose 4B beads (Pharmacia, Sweden) by the procedure described in B2 above. Plasminogen activator-fibronectin fragment conjugates were made up into separate solutions of known concentration containing from 16 to 160 units/ml of plasminogen activator activity. These solutions were then roller mixed for 2 hours at 4° C. with 100 mg (moist weight) quantities of the immobilised PFM described above. The immobilised PFM was then washed thoroughly with 50 mM TrisHCl solution, pH 7.6 to remove any unbound activity. The quantity of bound conjugate was then determined by direct assay of the PFM-Sepharose using the end point assay described in B5 above and aliquots of the affinity adsorbent in suspension. The activity of the plasminogen activator in both the starting material (plasminogen activator-fibronectin fragment conjugate) and in the washed PFM-Sepharose after binding was determined (in terms of units of plasminogen activator (PA) per ml in solution)

Figure 2:
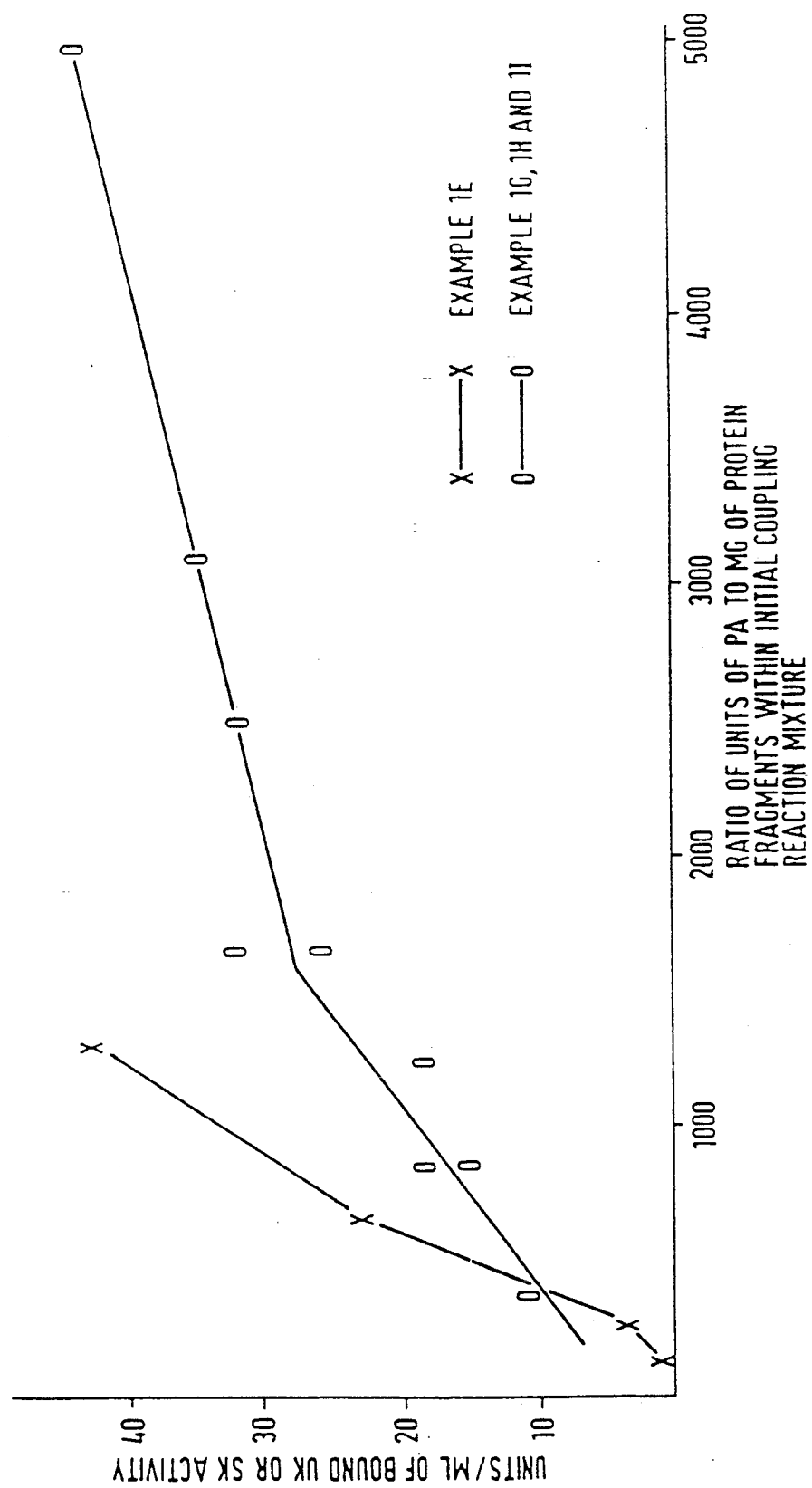
FIG. 2 shows the relationship for conjugates prepared by the procedures E and G–I between the amount of PA (in units) per mg fibronectin fragment used in the cross-linking reaction mixture that produced the conjugates and the amount of fibrin-binding PA which was produced in the conjugates.

The results of Table 9 are illustrated diagrammatically in FIGS. 1 and 2. FIG. 1 is a graph showing the correlation between the amount of conjugate added to the immobilised PFM and the amount of PA subsequently bound to it. FIG. 2 illustrates the relationship for conjugates prepared by the procedures of E and G–I above between the amount of plasminogen activator (in units) per mg fibronectin fragment used in the cross-linking reaction mixture that produced the conjugates and the amount of fibrin-binding plasminogen activator which was produced in the conjugates. Using urokinase there is a two-phase slope to the increase in conjugate PA content as more plasminogen activator was employed within the cross-linking reaction mixture. The slope with streptokinase is much steeper indicating more effective binding.

K. Binding of Plasminogen activator-fibronectin fragment conjugates to Sepharose 4B In order to establish that the plasminogen activator-fibronectin fragment conjugates were binding selectively to the fibrin monomer rather than to its support matrix, the product of method G above was applied to unsubstituted Sepharose 4B gel using the binding procedure outlined in J. The resultant fractions were assayed for plasminogen activator activity. The only activity to be found was in the unbound fractions. Recovery was 100%. Since the conjugate of method G had negligible affinity for unsubstituted Sepharose, it was concluded that a fibrin-substituted Sepharose behaved as a simulated fibrin clot and the conjugate bound entirely to the protein portion of the simulated clot.

L. Binding of unconjugated plasminogen activator to simulated blood clot tissue 2016 units of urokinase were made up into 2 ml of pH 7.3 buffer solution (20 mM Tris HCl containing 0.15 M NaCl) and applied to PFM-Sepharose 4B. The mixture was held at 4° C. for 2 hours. It was found that only 5% of the original UK activity present in solution became bound to the simulated clot, indicating that basal binding of unmodified urokinase to the simulated blood clot tissue was minimal.

M. Dissolution of fibrin-based clot tissue in response to plasminogen activators and plasminogen activator-fibronectin fragment conjugates The pharmacological efficacy of the plasminogen activator-fibronectin fragment conjugate product of method G was further tested by examining the lysis of fibrin-based clots in response to the selective binding of the conjugate. The influence of targetted plasminogen activator conjugates was assessed by measurement of $^{125}$I-FDPs released from $^{125}$I-labelled clots into the clot bathing medium.

Fibrinogen was iodinated by the chloramine T method (Green et al, *Biochem. J.*, (1963), 89, p.114) and activated using 100 U thrombin per gram fibrinogen. PBS - washed clot tissue was blotted into the form of a protein sheet from which small discs (10-20 mg) could be readily excised. $^{125}$I-Fibrin clot discs (20 mg) were incubated for 2hrs at room temperature in 0.25 ml, Tris buffer solution, pH 7.4 (50 mM Tris, 110 mM NaCl) containing either 800 U/ml urokinase or 800 U/ml urokinase-fibronectin fragment conjugate.

The clot discs were washed twice with 2 ml of Tris buffer solution, pH 7.4 to remove non-specifically bound urokinase. Control clot discs were incubated in Tris buffer solution, pH 7.4, without urokinase or conjugate and washed in parallel with test samples.

Clot discs were transferred to a chamber (10 ml vol.) through which the clot bathing medium (25 ml) was circulated from a reservoir at a flow rate of 2 ml/min. The bathing medium consisted of Tris buffer solution, pH 7.4, containing 0.03mg/ml plasminogen and 1 mg/ml human albumin.

Figure 3:
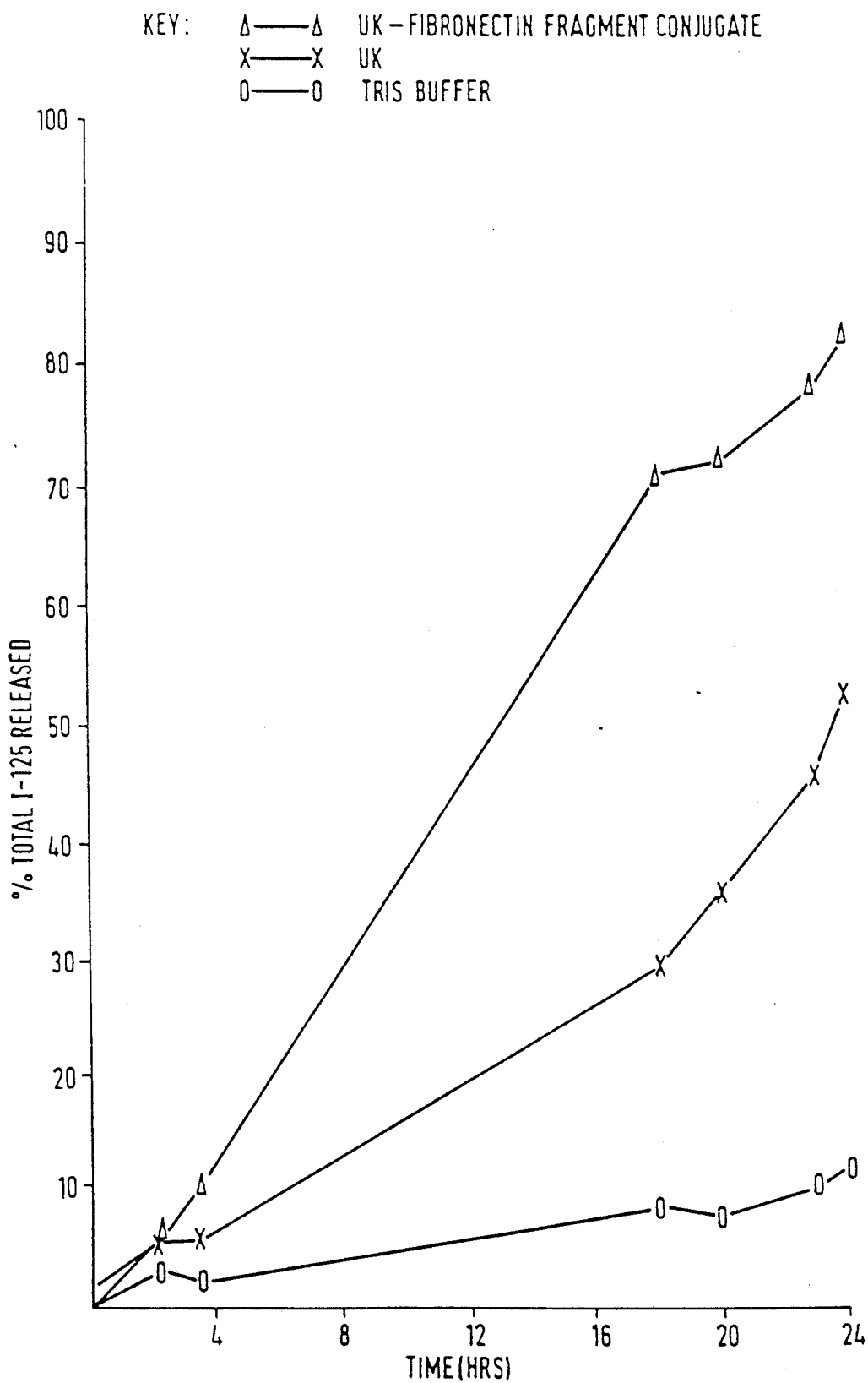
FIG. 3 shows the time course of $^{125}I$ radioactivity released from fibrin clot discs in response to urokinase activity.

Samples (0.5 ml) of the bathing medium were taken at intervals over a 24 hr period and solubilised radioactivity determined. The results of these measurements are represented diagrammatically in FIG. 3, which is a graph showing the time course of $^{125}$I radioactivity released from fibrin clot of discs in response to urokinase activity. Dissolution of the clots incubated with conjugate was up to 3.3 times faster (for example at 18 hrs: control = nil activator-stimulated lysis) than that with the equivalent activity of plasminogen activator alone. This indicated that specific and preferential binding of conjugate can enhance the activation of plasminogen in the vicinity of a clot and hence fibrinolytic breakdown of the clot.

EXAMPLE 2

PREPARATION OF ANTI-RHEUMATIC CONJUGATES

A. Direct Covalent Coupling of Gold to Fibronectin or Albumin

A1. Direct covalent coupling of gold to fibronectin fibronectin-Sepharose or albumin-Sepharose 1 ml of fibronectin-Sepharose slurry [1-2 parts coupling buffer (50 mM Tris-HCl, pH 7.5, 1 M urea) plus 1 part wet settled volume of gel consisting of 0.7 gm fibronectin/gm of CNBr-activated Sepharose 4B] plus 1 ml of coupling buffer containing 50 μM of sodium aurothiomalate were incubated with roller mixing for 4 hours at 37° C. The Sepharose was then washed with a suitable solution, for example 50 mM Tris-HCl, pH 7.5, to remove unreacted gold compound and protein. A moist pellet of gel was recovered either by centrifugation or by vacuum filtration through a glass sinter and incubated with trypsin at an enzyme to protein substrate ratio of approx 1:200 in 50 mM Tris-HCl, pH 7.5 for 15-120 mins at 37° C. Released gold-fibronectin fragment conjugate was separated from the Sepharose by centrifugation.

Albumin-Sepharose was substituted for fibronectin-Sepharose in the above procedure to obtain gold-albumin fragment conjugates.

Gold conjugates obtainable by the above procedures are suitable as carrier protein-gold conjugates for preparation of anti-rheumatic conjugates by cross-linking to gelatin-targetting adhesive protein fragments.

Conjugation of gold was also tested over a range of conditions (temperature, incubation time, ionic strength). The gold component of sodium aurothiomalate was followed specifically by atomic absorption spectroscopy and protein was measured by the Folin-Lowry assay. Table 10 below shows how the amount of bound gold varied. Binding (in μ moles of gold per unit volume of fibronectin-Sepharose) was significant but low (6-8 μM) in low ionic strength Tris-HCl. Addition of 1 M urea increased binding by between 50%-150% with the optimum at 4 hrs and 37° C. Table 11 below shows the relative effect of increasing levels of urea on binding gold to fibronectin-Sepharose. Increasing urea concentration between 0.1 and 1.0 M increased the gold incorporation by almost four fold (in this case gold binding was measured relative to the protein content of the conjugate). In fact, these are very high levels of binding of the order of $1.2 \times 10^4$ moles gold/mol fibronectin. When albumin-Sepharose was substituted for fibronectin-Sepharose, gold binding was approximately 35%, on a protein weight basis, of the minimum level for fibronectin-Sepharose. Although coupling was at low ionic strength, the final conjugate was largely stable to physiological NaCl levels. Loss of gold from the immobilised complex was constant at 21% to 23% between 0.1 M and 0.75 M NaCl.

TABLE 10

| Effect of reaction conditions on gold coupling to solid phase fibronectin | | | | | |
|---|---|---|---|---|---|
| | 50 mM Tris | 0.15 mM NaCl 50 mM Tris | | 1M Urea | |
| | μM Au[1] | μM Au | % of Basal[2] | μM Au | % of Basal |
| 2 hr reaction | | | | | |
| +4° C. | 6.00 | 4.65 | 77.5% | 9.15 | 152.5% |
| +37° C. | 7.20 | 3.60 | 50% | 12.75 | 177% |
| 4 hr reaction | | | | | |
| +4° C. | 6.75 | 6.30 | 93% | 12.00 | 178% |
| +37° C. | 7.80 | 6.30 | 81% | 19.50 | 250% |

(1) Figures refer to total Sepharose-bound gold (by atomic absorption) recovered from 2 ml of gel.
(2) Basal binding is taken as value in Tris buffer only, using corresponding conditions and taken as 100%

TABLE 11

| Influence of urea concentration on conjugation of gold to fibronectin-Sepharose | | |
|---|---|---|
| Urea Concentration | Mean Gold incorporation (μM/μg protein)* | % increase over control level |
| 0 | 0.05 | — |
| 0.1M | 0.098 | 96% |
| 0.5M | 0.133 | 165% |
| 1M | 0.20 | 390% |
| 2M | 0.193 | 287% |

*Mean of 2 experiments; incubation of 4 hrs at 37 C.

A2. Direct covalent coupling of gold to fibronectin or fibronectin fragments immobilised on fibronectin-Sepharose Fibronectin-Sepharose binds large quantities of soluble fibronectin at low ionic strength which can be recovered by raising the buffer NaCl concentration.

1 ml of fibronectin-Sepharose slurry [1–2 parts buffer (50 mM Tris-HCl, pH7.5) plus 1 part wet settled volume of gel consisting of 0.7mg fibronectin/gm of CNBr-activated Sepharose 4B] was mixed with 2 ml of purified plasma fibronectin (approx. 1 mg/ml) in the same buffer and mixed for 15–30 mins. The gel was washed (same buffer) to remove unbound fibronectin and incubated with roller mixing for 4 hrs at 37° C. in 50 mM Tris-HCl pH7.5 containing 1 M urea and 25 u mole of gold as sodium aurothiomalate per mg of fibronectin loaded. The gel was then again washed and resuspended in high ionic strength buffer (50 mM Tris-HCl pH7.5: 0.5 M NaCl) to dissociate the adsorbed fibronectin-gold conjugate. Mixing was carried out at room temperature for 15–60 mins. The gold-fibronectin conjugate in solution was de-salted by dialysis, ultrafiltration or gel filtration or a combination of such techniques and stored frozen or dry.

Using this technique for gold conjugation, 37% of the gold applied was conjugated to give a specific binding value of $9.8 \times 10^3$ moles gold/mole of fibronectin. After cross-linking to gelatin-targetting thrombin fragments of fibronectin (see section C), the specific gold binding was reduced to $1.1 \times 10^3$ mole gold/mole of fibronectin.

In the above procedure, soluble fibronectin may be replaced by fibronectin fragments to also provide carrier protein-gold conjugates suitable for preparation of anti-rheumatic conjugates by cross-linking to gelatin targetting adhesive protein fragments.

A3. Direct covalent coupling of gold to fibronectin in the presence of gelatin Using the gold conjugation methods described in A1 and A2 above, the resulting gold-fibronectin or gold-fibronectin fragment conjugates do not retain gelatin-binding activity. In this third method used for direct coupling of gold to fibronectin or fibronectin fragments, the gelatin-binding sites of the protein employed in the coupling reaction were protected by binding to gelatin either in the form of soluble gelatin or gelatin-Sepharose.

2 mls of a 1 to 5 mg/ml solution of gelatin (prepared by denaturation of purified skin collagen) in 50 mM Tris-HCl pH7.5 was mixed with 2 mg of intact fibronectin or gelatin-binding fibronectin fragments in the same buffer. The mixture was rolled for 1 hour at room temperature. Alternatively, the fibronectin or gelatin-binding fibronectin fragments were adsorbed on to gelatin-Sepharose in the same buffer. 50 μmoles of sodium aurothiomalate were added and the solution or gelatin-Sepharose-fibronectin slurry made up to 1 M with urea and mixed at room temperature for 4 hours.

Where soluble gelatin was used, the gelatin-fibronectin binding was disrupted by adding 4M urea, dialysing into 20 mM sodium phosphate containing 4 M urea at pH 5.2 and mixing with 1 gm of pre-swollen carboxymethyl cellulose ion-exchanger (Whatman CM52*). Soluble gelatin was bound to the ion-exchanger and removed by centrifugation leaving the soluble conjugate. ≠* trade mark Where gelatin-Sepharose was used, the fibronectin-gold conjugate was made on the gel and unreacted drug or protein fragment removed by washing with the same buffer free of gold compound. The final fibronectin-gold conjugate was recovered by washing the gelatin-Sepharose adsorbent either with 4 M urea or 1 M arginine in 50 mM Tris-HCl, pH 7.5.

Using a "gelatin binding protection method" as above with whole fibronectin, it was found possible to conjugate about 50% of the gold to give fibronectin-gold conjugate with $2.3 \times 10^3$M gold/M fibronectin.

From gelatin-binding gold-fibronectin fragment conjugates thus isolated, conjugates having an fibronectin fragment with gelatin-binding affinity, but lacking fibrin-binding affinity may be selected by FFFM-Sepharose or heparin-Sepharose affinity chromatography suitable for direct use as antirheumatic conjugates. It will be appreciated that such anti-rheumatic conjugates may also be obtained by subjecting gelatin-binding gold-whole fibronectin conjugates isolated by a procedure as above to protease digestion, with subsequent selection of gold-fibronectin fragment conjugates lacking fibrin-binding affinity. Alternatively gold-fibronectin conjugates, as well as gold-fibronectin fragment conjugates prepared by a "gelatin-binding protection method" as above, may be employed as carrier protein-gold conjugates for preparation of anti-rheumatic conjugates by cross-linking to gelatin-targetting adhesive protein fragments, e.g. fibronectin fragments having gelatin-binding affinity, but substantially lacking fibrin-binding affinity.

B. Preparation of Gelatin-Binding Fragments of Fibronectin Lacking Fibrin-Binding Affinity Fibronectin was digested with trypsin or thrombin as described in Sections C1 and C2 of Example 1 or with cathepsin D in conventional manner to yield a mixture of fragments with either or both gelatin-binding affinity and fibrin-binding affinity or neither of these two binding specificites. 10 ml of a 1 mg/ml solution of protease digested fibronectin in 50 mM Tris-HCl, pH 7.5 was applied to a heparin-Sepharose column. Unbound material (free of fragments with a heparin or fibrin binding site) was applied to a gelatin-Sepharose column at 1 mg/ml in 50 mM Tris-HCl, pH7.5 containing 0.5 M NaCl. After washing off unbound protein, gelatin-binding fragments were eluted with either 4 M urea or 1 M arginine in running buffer and desalted by dialysis.

C. Cross-linking of Carrier Protein-Gold Conjugates to Gelatin Targetting Fibronectin Fragments 5 ml of fibronectin carrier-gold conjugate (prepared by a procedure as described in A1, A2 or A3 above) in 10 mM sodium phosphate buffer pH 5.2 was made up to a final concentration of 1% (0.24 M) cyanamide and incubated at 22° C. for 1 to 4 hours with 5 ml of gelatin-binding fibronectin fragments prepared as in B above, at the same protein concentration as the fibronectin-gold conjugate. Excess reactants were removed by dialysis, ultra-filtration or gel filtration.

D. Testing for Gelatin Binding Activity of The Final Conjugate

The final conjugate was assayed for gelatin binding activity by applying it to a gelatin-Sepharose column as in B above. Bound material was eluted and assayed for total protein and for gold content. This gave a measure of gelatin-binding as μM of gold/μg gelatin-binding protein.

I claim:

1. A pharmaceutically active conjugate comprising an anti-rheumatic agent for treating rheumatic disease, wherein said anti-rheumatic agent is conjugated directly or indirectly with at least one fragment of fibronectin having improved gelatin-binding specificity compared with that of a whole parent fibronectin molecule, wherein said fibronectin fragment does not exhibit cell attachment activity.

2. A conjugate as claimed in claim 1 wherein the said anti-rheumatic agent is covalently conjugated.

3. A conjugate as claimed in claim 1 wherein the said anti-rheumatic agent is selected from gold, anti-rheumatic gold compounds and penicillamine.

4. A conjugate as claimed in claim 1 wherein the anti-rheumatic agent and said conectin fragment(s) are conjugated directly or indirectly to a carrier molecule.

5. A conjugate as claimed in claim 4 wherein the said carrier is selected from fibronectin or albumin.

6. A conjugate as claimed in claim 4 wherein the said carrier is covalently conjugated.

7. A method for treating a rheumatic disease in a human or non-human animal, comprising administering to said human or non-human animal by an effective route and in an effective amount a pharmaceutically active conjugate comprising a pharmaceutically active substance for treating said rheumatic disease, wherein said pharmaceutically active substance is conjugated directly or indirectly with at least one fragment of fibronectin having improved gelatin-binding specificity compared with that of a whole parent fibronectin molecule, wherein said fibronectin fragment does not exhibit cell attachment activity.

8. The method of claim 7, wherein said pharmaceutically active conjugate is administered to a human.

9. The method of claim 7, wherein said pharmaceutically active substance is selected from the group consisting of gold, anti-rheumatic gold compounds and penicillamine.

10. A method for preparing a pharmaceutically active conjugate for treating rheumatic disease, comprising the step of conjugating a pharmaceutically active substance directly or indirectly to at least one fragment of fibronectin, said fibronectin fragment having improved binding specificity for gelatin compared with that of a whole parent fibronectin molecule, wherein said fibronectin fragment does not exhibit cell attachment activity.

11. The method of claim 10, wherein said fibronectin fragment is a component of a protease digestion mixture of said a whole parent fibronectin molecule.

12. The method of claim 10, wherein said pharmaceutically active substance is covalently conjugated to a carrier, and said carrier is then covalently conjugated to one or more of said fibronectin.

13. The method of claim 10, wherein said pharmaceutically active substance is not a protein.

14. The method of claim 13 wherein said carrier is a protein containing sulphydryl groups.

15. The method of claim 14 wherein gold is directly conjugated to said carrier protein via said sulphydryl groups by reacting said carrier protein with aurothiomalic acid or a salt thereof.

16. The method of claim 15 wherein said carrier protein-gold conjugate is digested by a protease and a resultant protein-gold conjugate is covalently conjugated to said one or more fibronectin.

17. A method of preparing a pharmaceutically active conjugate for treating rheumatic disease, comprising the steps of:

(a) conjugating a pharmaceutically active, non-protein substance directly or indirectly to a whole parent fibronectin molecule to form a pharmaceutically active conjugate;

(b) digesting said pharmaceutically active conjugate with a protease; and (c) selecting a pharmaceutically active fibronectin fragment conjugate having improved gelatin-binding specificity compared to that of said whole parent fibronectin molecule wherein said fibronectin fragment does not exhibit cell attachment activity.

18. The method of claim 17 which further comprises protecting binding sites on the whole parent fibronectin molecule specific to said gelatin prior to proteolysis.

* * * * *